United States Patent
Noble et al.

(10) Patent No.: US 10,485,939 B2
(45) Date of Patent: Nov. 26, 2019

(54) METERED DOSE INHALER CANISTER AND SHROUD

(71) Applicant: Presspart Manufacturing Limited, Lancashire (GB)

(72) Inventors: Alan William Noble, Rossendale (GB); Antony Brian Cross, Clitheroe (GB)

(73) Assignee: Presspart Manufacturing Limited, Lancashire (GB)

( * ) Notice: Subject to any disclaimer, the term of this patent is extended or adjusted under 35 U.S.C. 154(b) by 0 days.

(21) Appl. No.: 15/764,514

(22) PCT Filed: Oct. 1, 2015

(86) PCT No.: PCT/GB2015/052882
§ 371 (c)(1),
(2) Date: Mar. 29, 2018

(87) PCT Pub. No.: WO2017/055786
PCT Pub. Date: Apr. 6, 2017

(65) Prior Publication Data
US 2018/0264210 A1    Sep. 20, 2018

(51) Int. Cl.
*A61M 15/00* (2006.01)
*B65D 83/38* (2006.01)
(Continued)

(52) U.S. Cl.
CPC ....... *A61M 15/009* (2013.01); *B05B 11/0038* (2018.08); *B65D 83/384* (2013.01); *A61M 11/00* (2013.01); *A61M 2207/00* (2013.01)

(58) Field of Classification Search
CPC .............. B65D 83/384; B65D 83/0094; B65D 83/0005; B65D 83/0055; B65D 83/0061;
(Continued)

(56) References Cited

U.S. PATENT DOCUMENTS 3,184,115 A    5/1965    Meshberg
4,593,836 A *  6/1986    Lilienthal ............ B65D 83/687
                                                                 222/135
(Continued)

FOREIGN PATENT DOCUMENTS

EP    0755877 A1    1/1997
GB    2267936 A  * 12/1993 ............. B65D 83/38
(Continued)

OTHER PUBLICATIONS

International Search Report and Written Opinion dated May 27, 2016 in corresponding PCT application No. PCT/GB2015/052882.
(Continued)

*Primary Examiner* — Tu A Vo
(74) *Attorney, Agent, or Firm* — Nields, Lemack & Frame, LLC

(57) ABSTRACT

A metered dose inhaler canister combination includes a canister constructed for containing a pharmaceutical composition, the canister having a canister base, a side wall extending from the canister base, an open end distal from the base and a first cooperating formation arranged at the open end and extending generally distally from the canister base; a shroud having a shroud base and a side wall extending from the shroud base to a waist, the base and side wall defining a vessel constructed to receive the canister therein, the waist defining an aperture of constricted width constructed to receive the canister therethrough, and a second cooperating formation extending generally distally from the waist, wherein the respective first and second cooperating formations adopt an engaged condition in which the canister is retained within the shroud.

17 Claims, 4 Drawing Sheets

(51) Int. Cl.
*B05B 11/00* (2006.01)
*A61M 11/00* (2006.01)

(58) Field of Classification Search
CPC ............ B65D 83/0066; B65D 83/0072; B65D 83/0083; B65D 83/0088; B65D 83/0409; B65D 83/0847; A61M 15/009; A61M 2207/00; B64D 83/00; B05B 11/0038
See application file for complete search history.

(56) References Cited

U.S. PATENT DOCUMENTS

| | | | | |
|---|---|---|---|---|
| 4,676,408 | A * | 6/1987 | Speitel | B65D 83/384 222/183 |
| 5,069,590 | A * | 12/1991 | Stoffel | B21D 51/24 413/1 |
| 5,878,917 | A * | 3/1999 | Reinhard | A61M 15/009 222/156 |
| 5,964,021 | A | 10/1999 | Stoffel | |
| 6,651,847 | B2 * | 11/2003 | Mekata | B65D 83/38 222/105 |
| 6,932,789 | B2 * | 8/2005 | Zierenberg | A61M 5/30 604/68 |
| 9,757,750 | B2 * | 9/2017 | Holakovsky | A61M 15/0065 |
| 10,016,568 | B2 * | 7/2018 | Bach | A61M 15/0065 |
| 2002/0195167 | A1 * | 12/2002 | Garcia | B05B 11/0038 141/173 |
| 2004/0079361 | A1 | 4/2004 | Clayton et al. | |
| 2006/0016449 | A1 * | 1/2006 | Eicher | A61M 15/0065 128/200.14 |
| 2006/0048843 | A1 * | 3/2006 | Yerby | B65D 83/38 141/20 |
| 2010/0129679 | A1 * | 5/2010 | Roeterdink | B21D 22/21 428/586 |
| 2013/0284759 | A1 * | 10/2013 | Teramoto | B65D 83/384 222/94 |
| 2014/0361038 | A1 * | 12/2014 | Mekata | B65D 83/384 222/95 |

FOREIGN PATENT DOCUMENTS

| | | |
|---|---|---|
| GB | 2525226 A | 10/2015 |
| JP | 2011-136747 A | 7/2011 |

OTHER PUBLICATIONS

International Preliminary Report on Patentability dated Feb. 26, 2018 in corresponding PCT application No. PCT/GB2015/052882.

* cited by examiner

METERED DOSE INHALER CANISTER AND SHROUD

This invention relates to metered dose inhalers in particular for pharmaceutical use and more especially to modified canisters suitable for use with such metered dose inhalers. Embodiments of the present invention relate to metered dose inhaler canisters of relatively small size in combination with a shroud. The shroud can be configured such that the external dimensions of the combined canister and shroud are greater, in at least one dimension, than those of the shroud, and in particular such that the combined canister and shroud have an external shape or profile which conforms to or mimics that of a conventionally sized metered dose inhaler canister.

BACKGROUND

Metered dose inhalers and canisters for metered dose inhalers have been known for many years. It has also been known to provide canisters for metered dose inhalers in a range of sizes so that, for example, different numbers of doses can be dispensed from the differently sized canisters.

Developments in pharmaceutical formulations to be contained in metered dose inhaler canisters have lead to a demand for relatively smaller canisters. In part such demand has arisen from the provision of new pharmaceutical formulations which can require a smaller total volume of the formulation to be contained in the MDI canister. It has been appreciated that satisfactory results are not always attained simply by filling a standard sized MDI canister with a smaller volume of pharmaceutical formulation and that, to the contrary, it can be necessary for accurate dosing of the pharmaceutical formulation to match the size of the MDI canister to the required volume of the pharmaceutical formulation. WO02/056949 contains a useful discussion of the reasons for using smaller MDI canisters and the contents thereof are incorporated herein by reference, in particular page 2 lines 1 to 32.

WO02/056949 describes a shroud for a relatively smaller MDI canister which is provided in order to increase the effective external volume of the canister. The shroud can be in the form of a "cut down" conventional MDI canister into which the relatively smaller MDI canister is received. The shroud can be formed with an inwardly directed circumferential bead which limits the extent to which the relatively smaller MDI canister can penetrate into the shroud. In one version, the shroud can be secured to the relatively smaller canister only by an interference fit between a cylindrical inner wall of the shroud and a juxtaposed cylindrical outer wall of the relatively smaller MDI canister.

In another version as illustrated in FIG. 1, a complete relatively larger MDI can is used as the shroud. As shown in FIG. 1, the shroud 20 of this version of WO02/056949 can be in the form of an MDI canister of larger size than the canister 4 in which the aerosol formulation (i.e. the pharmaceutical formulation) is contained. The relatively smaller canister 4 can comprise a circular base 6 and a cylindrical sidewall 8 extending from the base to an open end 32. The open end 32 can comprise a circumferential flange 34 which is dimensioned to extend over the neck 21 of the relatively larger MDI canister (shroud) 20. The valve ferrule 18 can be crimped over neck 21, so trapping the circumferential flange 34 between the ferrule and the neck 21, and securing the relatively smaller MDI canister 4 within the shroud 20. A gasket seal 19 can be provided to form a seal with the circumferential flange 34.

Embodiments of the present invention seek to provide an MDI canister and a shroud which, in combination overcome, or at least mitigate, some disadvantages of the prior art. In embodiments of and variations of the invention such a combination can have an external profile which is similar to, and preferably substantially the same as, that of a conventional (relatively larger) MDI canister. In this way, modification of assembly machinery for the manufacture of the MDI is not required. Also, modification of the conventional housing into which an MDI fits for patient use can be obviated and patient expectations can be met. Patient compliance can also be enhanced.

Further, in embodiments of the invention different sizes of the relatively smaller MDI canister can be used in order to define internal volumes appropriate for different pharmaceutical formulations, while maintaining the same external profile of the combination.

Also, in embodiments of the invention secure mounting of the relatively smaller MDI canister within the shroud can be achieved, with little or no relative movement between the relatively smaller MDI canister and the shroud when so mounted. Such secure mounting can be achieved before attachment of the MDI valve to the combination and before filling of the combination with pharmaceutical formulation. Handling of the combined canister and shroud on a production line can thereby be facilitated.

BRIEF SUMMARY OF THE DISCLOSURE

In accordance with the present inventions there is provided a metered dose inhaler canister combination comprising a canister configured for containing a pharmaceutical composition, the canister having a canister base, a side wall extending from the canister base, an open end distal from the base and a first cooperating formation arranged at said open end and extending generally distally from said canister base;

a shroud having a shroud base and a side wall extending from the shroud base to a waist, the base and side wall defining a vessel configured to receive the canister therein, the waist defining an aperture of constricted width configured to receive the canister therethrough, and a second cooperating formation extending generally distally from said waist, wherein the respective first and second cooperating formations adopt an engaged condition in which the canister is retained within the shroud.

In some preferred embodiments the combined canister and shroud can have an external shape or profile which conforms to or mimics that of a conventionally sized metered dose inhaler canister.

When the respective first and second cooperating formations adopt the engaged condition in which the canister is retained within the shroud, the canister can be retained in fixed relation to the shroud. That is, in normal use or handling of the canister combination, the canister and shroud are held together by the cooperating formations such that the canister is within (preferably wholly within) the shroud and does not move with respect to the shroud.

In some preferred embodiments the internal profile of said aperture can be complementary to the external profile of said canister such that the canister is a sliding or clearance fit through the aperture. The canister can be in contacting relation at the aperture with a wall defining the aperture such that said aperture defining wall can also facilitate the holding of the canister in fixed relation to the shroud.

In some preferred embodiments the canister can be cylindrical and the aperture can be circular. In such embodiments, the external diameter of the canister can be substantially the same as the internal diameter of the aperture.

In other embodiments the canister can be other than cylindrical, such as ellipsoidal or polygonal in cross-section and the aperture can have a corresponding shape. For example, if the cylinder is ellipsoidal, the aperture can also be ellipsoidal.

In some preferred embodiments the respective first and second cooperating formations can be substantially annular.

In some preferred embodiments at least one of the first and second cooperating formations can be resiliently deformable for bringing said cooperating formations into said engaged condition.

In some preferred embodiments the first and second cooperating formations, when engaged, together can define an outwardly convex annular collar.

In some preferred embodiments the second cooperating formation can extend directly (that is, without any intervening component or portion) from said waist.

In some preferred embodiments said waist and outwardly directed collar can correspond to or mimic the shape of a corresponding waist and collar formed by a conventional metered dose inhaler canister, at which a valve containing ferrule can be attached. In particular, a ferrule can be crimped or otherwise deformed into engagement with an underside part of said collar. In this way, a ferrule can be attached to the canister combination of the invention without the need for any, or any substantial, modification of manufacturing equipment. In this respect, manufacturing equipment refers to bulk manufacturing equipment capable of manufacturing MDIs in numbers of hundreds or thousands or more per day, as distinct from bench tools and equipment suitable for making one off or low numbers of sample MDIs.

In some preferred embodiments said second cooperating formation can comprise a flange portion extending outwardly from said waist and a wall portion extending from said flange portion distally with respect to said shroud base.

In some preferred embodiments said first cooperating formation can comprise a flange portion extending outwardly from said cylindrical side wall and a wall portion extending from said flange portion distally with respect to said canister base.

In some preferred embodiments said first cooperating formation can further comprise an inwardly directly lip portion extending from a distal end of said wall portion.

In some preferred embodiments, when the first and second cooperating formations are in the engaged condition the respective wall portions of the first and second cooperating formations can be juxtaposed. In some preferred embodiments said respective wall portions can be in contacting relation.

In some preferred embodiments the shroud side wall can include a first wall portion which can extend from the shroud base and a shoulder portion which can extend from said first wall portion to said waist.

In some preferred embodiments the shroud side wall can include an inclined shoulder portion extending from a limit of said upright portion which is distal to the base to said waist. Said shoulder portion can slope inwardly from side wall. In some embodiments, shoulder portion can comprise a first (lower) shoulder part which is less steeply inclined and a second (upper) part which is more steeply inclined. Other shoulder parts of greater or lesser relative inclination can be included in the shoulder portion.

In some preferred embodiments said first wall portion of the shroud can extend substantially parallel to the longitudinal axis of the shroud. In some preferred embodiments, said first wall portion can be substantially cylindrical.

In some preferred embodiments said shroud can include a vent orifice which allows communication between the shroud exterior and shroud interior. In some preferred embodiments said vent orifice can comprise a hole disposed in the shroud proximate said waist.

In some preferred embodiments one of, or both of, the canister and the shroud can be formed from metal. In some preferred embodiments one of, or both of, the canister and the shroud can be formed of a deep drawn metal.

According to a second aspect of the present invention there is provided a metered dose inhaler comprising a metered dose inhaler canister combination according to the first aspect of the invention in combination with a ferrule containing a metering valve, said ferrule being attached to the canister combination at or proximate the open end of the canister, and wherein the valve communicates with the interior of the canister.

In some preferred embodiments the ferrule can be attached to the canister combination by crimping said ferrule around said engaged first and second cooperating formations.

In some preferred embodiments the metered dose inhaler can further comprise a pharmaceutical formulation including at least one pharmaceutical active contained within the canister.

According to a third aspect of the present invention there is provided a method of making a metered dose inhaler including the steps of forming a metered dose inhaler canister combination according to the first aspect of the invention by inserting the canister into the shroud until the respective first and second cooperating formations achieve the engaged condition, and securing a ferrule to the canister combination by engagement of the ferrule with an external part of said first and/or second cooperating formation.

In some preferred embodiments the ferrule can be crimped or otherwise deformed into engagement with said external part of said first and/or second cooperating formation.

BRIEF DESCRIPTION OF THE DRAWINGS

Embodiments of the invention are further described hereinafter with reference to the accompanying drawings, in which.

DETAILED DESCRIPTION

Figure 1:
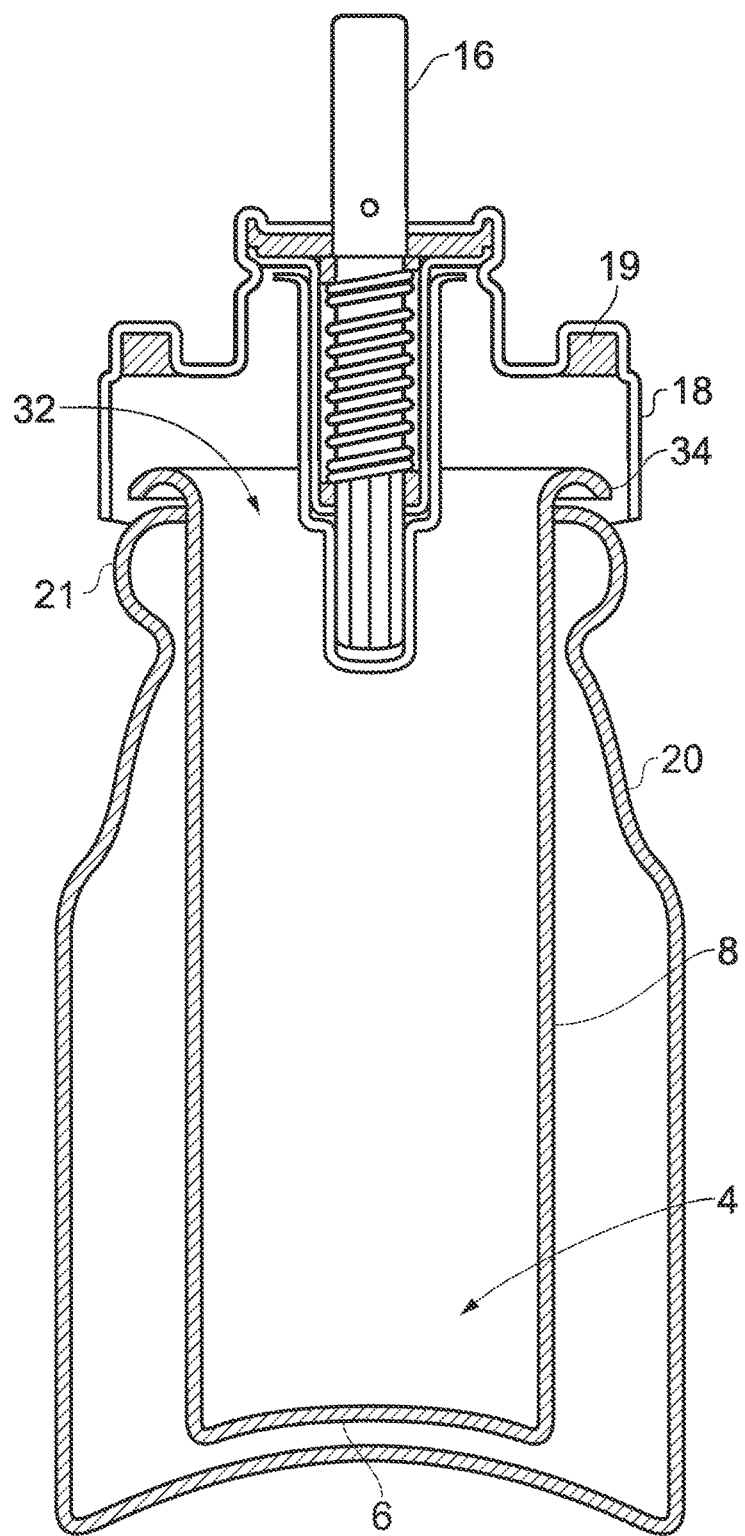
FIG. 1 is a cross section through a combination of an MDI canister and a shroud according to WO 02/056949.
Figure 2:
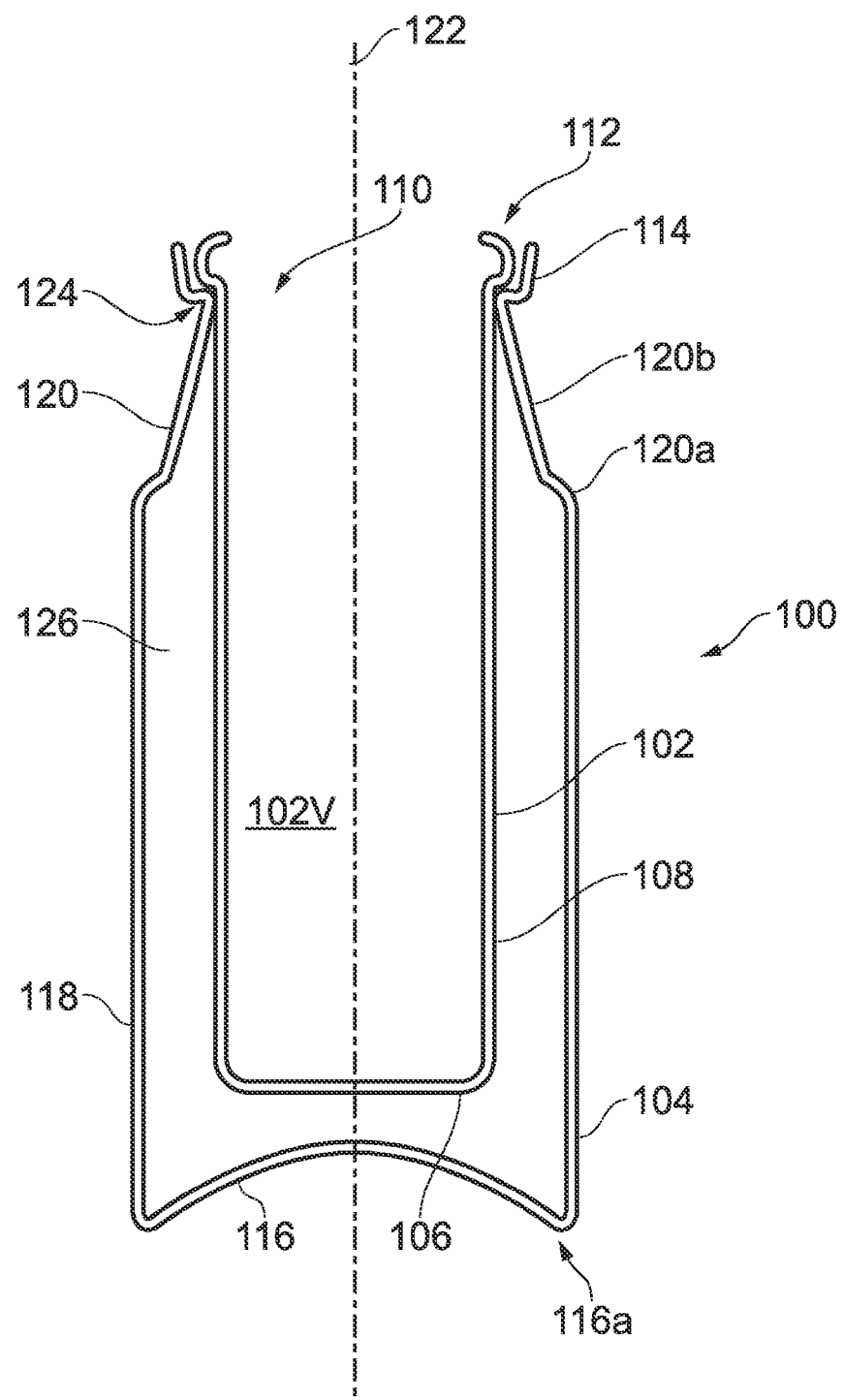
FIG. 2 is a schematic section through a canister combination according to an embodiment of the invention.

Referring now to FIGS. 1 and 2, the metered dose inhaler canister combination 100 according to embodiments of the invention comprises a canister 102 and a shroud 104. In the combination, the canister 102 is contained within the shroud 104. In particular, in the combination, the canister 102 is contained almost wholly within the shroud. Preferably a portion of the first engaging formation of the canister may extend outwardly to a small extent beyond the upper end or edge of the second engaging formation (of the shroud).

Canister 102 comprises a base 106 from which extends a side wall 108. Base 106 can be (but is not necessarily) substantially planar. Side wall 108 extends upwardly away from the base 106 (in the orientation of the canister combination as illustrated) and is preferably substantially cylindrical. Other shapes, such as polygonal or ellipsoidal shapes are not, however, excluded. Base 106 and side wall 108 define an internal volume 102V of the canister 102 in which a pharmaceutical formulation including a pharmaceutical active can be contained.

Canister 102 has an open end 110 at an upper end thereof (with respect to the illustrated orientation), that is, distal from the base 106. In use, open end 110 can accommodate portions of a metering valve (not shown in FIG. 2) whereby the metering valve can communicate with the interior of the canister. The construction and operational details of metering valves for metered dose inhalers are, as such, well known to the person of ordinary skill in the art and need not be further described here. In general terms, a suitable metering valve selected by the skilled person from those conventionally used for metered dose inhalers can be used with the canister combination of the invention. The selection of a particular metering valve suitable for particular circumstances (such as a particular pharmaceutical active or combination of actives, and a particular dosage amount) is within the knowledge of the person of ordinary skill in the art of metered dose inhalers.

Canister 102 is provided at its upper, open, end with a first cooperating formation 112 which cooperates with a second cooperating formation 114 of the shroud (as will be described below) in retaining the canister 102 in a substantially fixed location within the shroud 104, such that in normal use the canister 102 does not move with respect to the shroud.

Shroud 104 comprises a base 116 from which extends a side wall 118. In some preferred embodiments, base 116 can be (but is not necessarily) of dished form, so that the base forms a generally concave recess. Such a dished form can be advantageous in enhancing the strength of the shroud 104. In other embodiments, base 116 can be substantially planar. Where base 116 is of dished form, preferably the base 116 includes an outer ridge 116a on which the shroud can stably stand on a substantially planar surface.

A first portion of side wall 118 extends upwardly away from the base 116 (in the orientation of the canister combination 100 as illustrated). In some preferred embodiments first portion of side wall 118 can be substantially cylindrical. In some other embodiments, side wall 108 can be oval or polygonal (such as hexagonal) in lateral cross section.

At an upper end (with respect to the orientation shown in FIG. 2) of the first portion of the side wall 118 of shroud 104, a shoulder portion 120 can extend from the side wall 118. Shoulder portion 120 slopes inwardly from side wall 118, that is, generally towards the longitudinal axis 122 of the shroud 104. In some embodiments, shoulder portion 120 can conveniently comprise a first (lower) shoulder part 120a which is less steeply inclined and a second (upper) part 120b which is more steeply inclined. Other shoulder parts of greater or lesser relative inclination can be included in the shoulder portion 120.

At its upper end (with respect to the orientation shown in FIG. 2), that is, distal from base 116, side wall 118 (more particularly in some preferred embodiments, shoulder portion 120 of side wall 118) terminates at a waist 124 which constitutes the laterally narrowest portion of the shroud 104. In some preferred embodiments waist 124 can define an opening or aperture through which the side wall 108 of the canister 102 can pass to receive the canister 102 into the shroud 104.

In preferred embodiments where the side wall 108 of the canister is cylindrical, said aperture is circular. In embodiments where the side wall 108 of the canister is other than cylindrical, the shape of the aperture can conform to the external shape of the canister side wall 108.

In embodiments where the side wall 118 of the shroud 104 is other than cylindrical, shoulder portion 120 can be shaped to change from the non-cylindrical configuration of the side wall 108 to a circular or cylindrical configuration (or other configuration depending on the particular shape of the canister) at least at waist 124. In some preferred embodiments where the aperture is circular and the canister is cylindrical, the external diameter of the side wall 108 of the canister 102 is substantially the same as the internal diameter of waist 124 so that canister 102 is a clearance or sliding fit with the waist 124.

Shroud 104 is provided at its upper, open, end with a second cooperating formation 114 which cooperates with the first cooperating formation 112 of the canister 102 in retaining the canister 102 in a substantially fixed positional relationship with respect to the shroud 104, such that in normal use (including during manufacture of the MDI) the canister 102 does not move with respect to the shroud 104. In some preferred embodiments, the first and second cooperating formations 112, 114 can be configured to achieve a "snap fit" into their engaged condition, that is, when the canister 102 is received into the shroud 104 to the desired extent, which is typically the fullest extent to which the canister 102 can be so received. In the engaged condition of the respective first and second cooperating formations 112, 114, retain the canister 102 and shroud 104 in substantially fixed relation to one another, so that the canister 102 cannot be released from the shroud 104 in normal use of the canister combination 100 as part of a metered dose inhaler, or in the manufacture of a metered dose inhaler. If, unusually, the canister 102 is to be removed from the shroud 104, a substantial separating force is required to overcome the engagement of the respective first and second cooperating formations 112, 114.

When canister 102 is received within the shroud 104, shroud 104 can define an essentially closed container or vessel surrounding the canister 102. Thus, a void 126 is defined between outer surface of side wall 108 of canister 102 and inner surface of side wall 118 of the shroud 104. Void 126 can also exist between the respective bases 106, 116 of the canister 102 and shroud 104.

Figure 3:
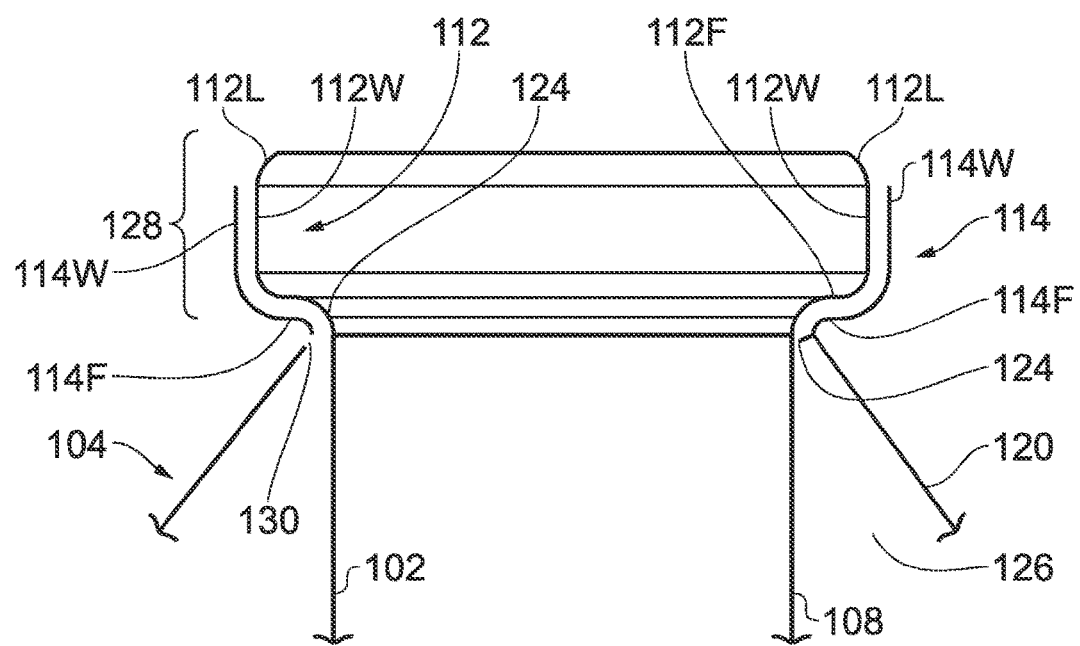
FIG. 3 shows in more detail the respective first and second engagement formations of the canister and the shroud according to some embodiments of the invention.

The cooperation of the first and second cooperating formations according to embodiments of the invention can be seen in more detail in FIG. 3. It should be noted that in FIG. 3 the spacing between the first and second cooperating formations 112, 114 is exaggerated for clarity of illustration.

As can be seen in particular from FIG. 3, second cooperating formation can comprise a shaped or profiled wall extending from said waist 124. In preferred arrangements, said shaped or profiled wall can be externally convex. The said shaped or profiled wall of the second cooperating formation 114 can comprise a flange portion 114F extending outwardly from said waist and a substantially upright wall portion 114W extending from said flange portion 114F distally with respect to said shroud base 116 to an upped edge or end of said second cooperating formation. Preferably said upper end or edge of the second cooperating formation can represent an upper limit of the shroud 104.

In some preferred embodiments a generally planar part of flange portion 114F can extend substantially radially outwardly with respect side wall 118, that is, substantially perpendicularly with respect to side wall 118. The term "substantially radially" can include exactly radially or an upward or (sometimes less preferably) downward inclination to the horizontal of said generally planar part (as measured at an external surface thereof) of not more than about 30° or 20°, such as not more than about 10° or not more than about 5°. In some embodiments said flange portion can be curved.

In some embodiments, upright wall portion 114W can extend from said flange portion to include a substantially cylindrical wall portion arranged substantially parallel to said side wall 118. In variations, said upright wall portion 114W may be configured to slope inwardly to a small extent such as at an inclination to the vertical of 5° or less such as 3° or 2° or 1°. In some variations said upright wall portion 114W can have a curved form and in some variations can represent a smooth continuation of said flange portion 114F.

The first cooperating formation can comprise a shaped or profiled wall extending from and upper limit of canister side wall 108. In preferred arrangements, said shaped or profiled wall can be externally convex. The said shaped or profiled wall of the first cooperating formation 112 can comprise a flange portion 112F extending outwardly from said cylindrical side wall 108 and a substantially upright wall portion 112W extending from said flange portion 112F distally with respect to said canister base 106. In some preferred embodiments a generally planar part of flange portion 112F can extend substantially radially outwardly with respect side wall 108, that is, substantially perpendicularly with respect to side wall 108. The term "substantially radially" can include exactly radially or an upward or (sometimes less preferably) downward inclination to the horizontal of said generally planar part (as measured at an external surface thereof) of not more than about 30° or 20°, such as not more than about 10° or not more than about 5°. In some embodiments said flange portion 112F can be curved.

In some embodiments, upright wall portion 112W can extend from said flange portion 112F to include a substantially cylindrical wall portion arranged substantially parallel to said side wall 108. In variations, said upright wall portion 112W may be configured to slope inwardly to a small extent such as at an inclination to the vertical of 5° or less such as 3° or 2° or 1°. In some variations said upright wall portion 112W can have a curved form and in some variations can represent a smooth continuation of said flange portion 112F.

In some preferred embodiments the said shaped or profiled wall of the first cooperating formation 112 can further comprise an inwardly directly lip portion 112L extending inwardly from a distal end of said wall portion 112W. In some variations said lip portion 112L can represent a smooth continuation of said upright wall portion 112W.

When the respective first and second cooperating formations adopt their engaged condition (as illustrated) the respective said shaped or profiled walls thereof (or at least parts of said walls) can be arranged in confronting relation, and in some preferred embodiments in contacting relation. In particular, flange portion 112F of the first cooperating formation 112 can be arranged in confronting relation, and in some preferred embodiments in contacting relation, with the flange portion 114F of the second cooperating formation 114. Thus the flange portion 114F can act to limit the extent of the passage of the canister 102 into the shroud 104 since when the respective flange portions 112F and 114F achieve contacting relation, further passage of the canister 102 into the shroud 104 is prevented.

In some preferred embodiments respective wall portions 112W and 114W are arranged in confronting relation (and advantageously in contacting relation) when the first and second cooperating formations 112, 114 adopt their engaged condition.

Figure 4:
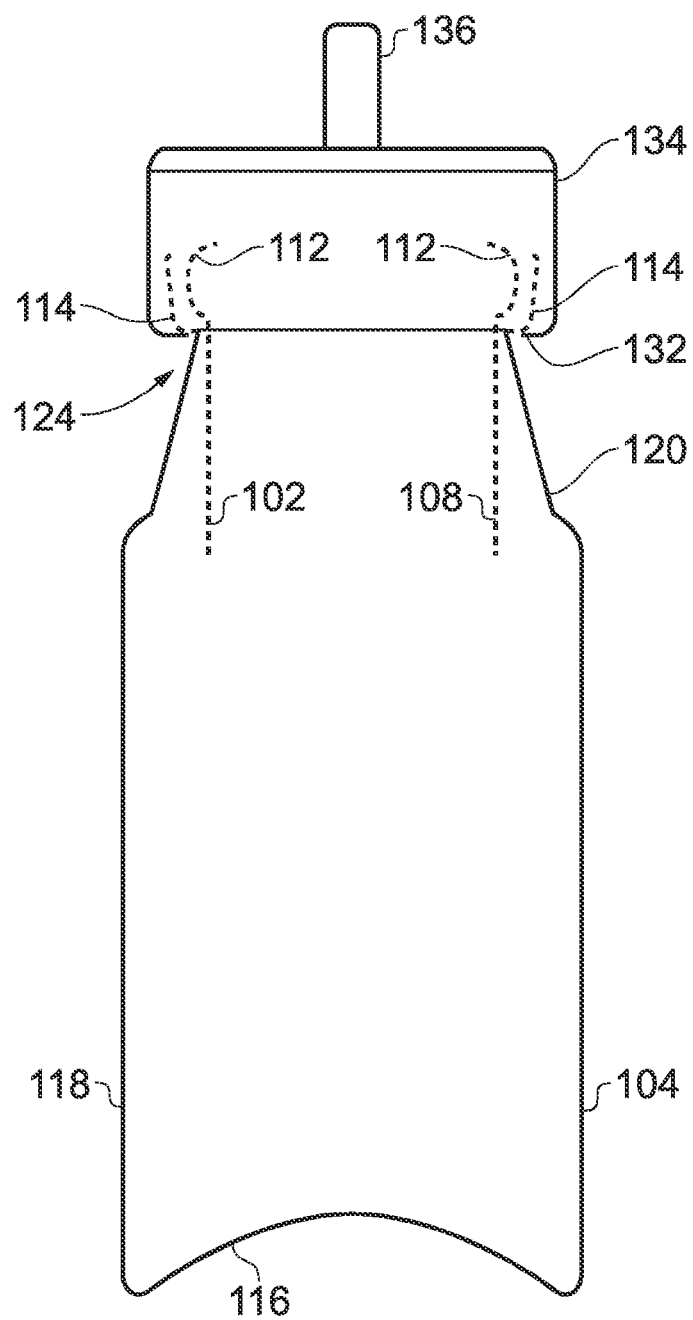
FIG. 4 shown a metered dose inhaler incorporating a canister combination according to one embodiment of the invention'

The respective first and second cooperating formations, when in their engaged condition can have the external profile of an externally convex annular collar 128. Collar 128 is outwardly or externally convex in at least the sense that parts thereof project generally radially outwardly from the waist 124. The profile of the collar 128 is advantageously such as to permit a valve ferrule 134 containing the metering valve (a valve stem 136 of which is shown in FIG. 4) to be fixedly attached to the canister combination 100 by crimping a portion 132 of the ferrule 134 around the collar 128. In particular, parts 132 of the ferrule 134 can be deformed into engagement with (i.e. crimped onto) flange portion 114F, such that removal of the ferrule 134 from the combination 100 is prevented in normal conditions of use. In this respect, the canister combination 100 can adopt an external profile which corresponds to or mimics that of a conventional metered dose inhaler canister of a usual volume as known from the prior art. In this way, a smaller volume can be defined (by the canister 102) for containing the pharmaceutical formulation—as can be advantageous when a smaller number of doses or a smaller volume of each dose is required—while at the same time presenting a profile for the canister combination which does not differ significantly from that of a conventional metered dose inhaler canister. In this way the canister combination 100 can be handled on or by conventional MDI manufacturing equipment, such as for filling of the canister 102 with the pharmaceutical formulation and or attachment of the ferrule containing the metering valve without any adaption, or without any significant adaption, of such manufacturing equipment. Also, by maintaining a conventional profile of the canister combination 102 which conforms to that of a conventional MDI canister, the canister combination 102 can be used in conventional MDI housings or actuators which are well known to, and well accepted by, patients, again without any, or any significant, modification thereof. In embodiments of the present invention the above embodiments can be achieved while facilitating easy insertion of the canister 102 into the shroud 104 and while easily achieving a secure and reliable connection between the canister 102 and the shroud 104 (by way of the respective cooperating formations) which hold the canister 102 in fixed relation to the shroud.

It is noted that different applications (such as different pharmaceutical formulations) may require different internal volumes for the canister 102. The volume of the canister 102 can be chosen by selecting a canister 102 of appropriate longitudinal dimension (i.e. appropriate length). The width (diameter) of the canister 102 is not varied, in order to maintain the desired fit with the waist 124 of the shroud 104. The variation in the length of the canister 102 (by selection of a canister 102 of appropriate length) is possible because the canister 102 is secured to the shroud 104 only at its top portion, specifically by the first cooperating formation 112. Of course, in possible embodiments of the combination 100 where providing an external profile of the combination 100 which corresponds to the profile of an conventional MDI canister is not important, the diameter of the waist 124 of the shroud 104 can be configured to conform to the diameter of a selected canister 102.

It is further noted that when the canister 102 and shroud 104 are positioned with respect to each other so that the first and second cooperating formations are in the engaged condition, the canister 102 is maintained in fixed positional arrangement with respect to the shroud 104 by the engagement of the cooperating formations 112, 114 and without the need for intervention by any other entity. For example, the canister combination 100 does not rely on the attachment of the ferrule by crimping for attachment of the canister to the shroud and in order to maintain the canister and shroud in their desired relative positions. Further, no processing step such as crimping is necessary at any stage for attachment of the canister 102 to the shroud 104, since the action of inserting the canister to the required extent into the shroud is sufficient to achieve engagement of the first and second cooperating formations. It follows that the canister is already held in fixed relation to the shroud at the time at which the ferrule is crimped into attachment with the canister combination 100.

Metered dose inhalers are necessarily subject to stringent efficacy and safety requirements set by national or regional regulatory authorities. One such requirement can be a leakage test. It is self evident that if the MDI suffers a leakage, such as of the propellant used for delivery of the pharmaceutical formulation and/or of the pharmaceutical formulation itself, accurate dosing of the pharmaceutical formulation to a patient is not achievable. One testing process for leakage from an MDI involves the immersion of the MDI in a water bath containing warm water, typically at about 50° C. to 60° C. Leakage of the MDI can then be detected visually or by weighing the MDI before and after immersion in the water bath, for example. However, such a water bath test is typically useful only when a path exists for leaked product from the canister of the MDI to the exterior of the MDI. The presence of a shroud, such as shroud 104 according to the invention, can mean that such a path from the canister to the exterior is not present. Accordingly, in some advantageous embodiments of the invention, the shroud 104 is provided with a vent orifice 130 which communicates with the exterior of the MDI and with the void 126 which exists between the canister 102 and the shroud 104. Any leakage of the contents of the canister into the void 126 can therefore be determined because of consequential escape of air or pharmaceutical formulation via the vent orifice 130. In some preferred arrangements, the vent orifice 130 is arranged immediately below the collar 128, that is, immediately below the engaged first and second cooperating formations 112, 114. Vent orifice 130 can take the form of a through hole formed in the shroud, typically having a diameter of less than 1 mm, such as about 0.5 mm.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A metered dose inhaler canister combination comprising:
   a canister configured for containing a pharmaceutical composition, the canister having a canister base, a side wall extending from the canister base, an open end distal from the base and a first cooperating formation arranged at said open end and extending generally distally from said canister base;
   a shroud having a shroud base and a side wall extending from the shroud base to a waist, the base and side wall defining a vessel configured to receive the canister therein, the waist defining an aperture of constricted width configured to receive the canister therethrough, and a second cooperating formation extending generally distally from said waist,
   wherein the respective first and second cooperating formations adopt an engaged condition in which the canister is retained within the shroud,
   wherein:
   said shroud includes a vent orifice which allows communication between a shroud exterior and a shroud interior,
   said first cooperating formation comprises a flange portion extending outwardly from said side wall and a wall portion extending from said flange portion distally with respect to said canister base,
   said second cooperating formation comprises a flange portion extending outwardly from said waist and a wall portion extending from said flange portion distally with respect to said shroud base,
   when the first and second cooperating formations are in the engaged condition the respective wall portions of the first and second cooperating formations are in contacting relation; and
   wherein both of the canister and the shroud are formed of a deep drawn metal.

2. A metered dose inhaler canister combination as claimed in claim 1, wherein said aperture has an internal profile and said canister has an external profile, and wherein the internal profile of said aperture is complementary to the external profile of said canister such that the canister is a sliding or clearance fit through the aperture.

3. A metered dose inhaler canister combination as claimed in claim 2, wherein the canister is cylindrical and has an external diameter, and the aperture is circular and has an internal diameter, the external diameter of the canister being substantially the same as the internal diameter of the aperture.

4. A metered dose inhaler canister combination as claimed in claim 1, wherein the canister is cylindrical and has an external diameter, and the aperture is circular and has an internal diameter, the external diameter of the canister being substantially the same as the internal diameter of the aperture.

5. A metered dose inhaler canister combination as claimed in claim 1, wherein the respective first and second cooperating formations are substantially annular.

6. A metered dose inhaler canister combination as claimed in claim 1, wherein at least one of the first and second cooperating formations is resiliently deformable for bringing said cooperating formations into said engaged condition.

7. A metered dose inhaler canister combination as claimed in claim 1, wherein the first and second cooperating formations, when engaged, together define an outwardly convex annular collar.

8. A metered dose inhaler canister combination as claimed in claim 1, wherein said first cooperating formation further comprises an inwardly directly lip portion extending from a distal end of said wall portion.

9. A metered dose inhaler canister combination as claimed in claim 8, wherein when the first and second cooperating formations are in the engaged condition the respective wall portions of the first and second cooperating formations are juxtaposed.

10. A metered dose inhaler canister combination as claimed in claim 1, wherein when the first and second cooperating formations are in the engaged condition the respective wall portions of the first and second cooperating formations are juxtaposed.

11. A metered dose inhaler canister combination as claimed in claim 1, wherein said vent orifice comprises a hole disposed in the shroud proximate said waist.

12. A metered dose inhaler comprising a metered dose inhaler canister combination as claimed in claim 1 in combination with a ferrule containing a metering valve, said ferrule being attached to the canister combination at or proximate the open end of the canister, and wherein the canister has an interior and the valve communicates with the interior of the canister.

13. A metered dose inhaler as claimed in claim 12, wherein the ferrule is attached to the canister combination by crimping said ferrule around said engaged first and second cooperating formations.

14. A metered dose inhaler as claimed in claim 13, further comprising a pharmaceutical formulation including at least one pharmaceutical active contained within the canister.

15. A metered dose inhaler as claimed in claim 12, further comprising a pharmaceutical formulation including at least one pharmaceutical active contained within the canister.

16. A method of making a metered dose inhaler comprising the steps of forming a metered dose inhaler canister combination as defined in claim 1 by inserting the canister into the shroud until the respective first and second cooperating formations achieve the engaged condition and securing a ferrule to the canister combination by engagement of the ferrule with an external part of said first and/or second cooperating formation.

17. A method as claimed in claim 16, wherein the ferrule is crimped or otherwise deformed into engagement with said external part of said first and/or second cooperating formation.

* * * * *